(12) United States Patent
Kosonen et al.

(10) Patent No.: US 10,456,082 B2
(45) Date of Patent: Oct. 29, 2019

(54) METHOD AND APPARATUS FOR CONTACTING SKIN WITH SENSOR EQUIPMENT

(71) Applicant: Nokia Technologies Oy, Espoo (FI)

(72) Inventors: Matti Kosonen, Järvenpää (FI); Harri Lasarov, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/529,565

(22) PCT Filed: Nov. 19, 2015

(86) PCT No.: PCT/FI2015/050805
§ 371 (c)(1),
(2) Date: May 25, 2017

(87) PCT Pub. No.: WO2016/083665
PCT Pub. Date: Jun. 2, 2016

(65) Prior Publication Data
US 2017/0319136 A1 Nov. 9, 2017

(30) Foreign Application Priority Data
Nov. 28, 2014 (EP) ..................................... 14195295

(51) Int. Cl.
*A61B 5/00* (2006.01)
*G06F 1/16* (2006.01)
*G06F 3/01* (2006.01)

(52) U.S. Cl.
CPC ............ *A61B 5/6844* (2013.01); *A61B 5/681* (2013.01); *A61B 5/6803* (2013.01);
(Continued)

(58) Field of Classification Search
CPC ..... A61B 5/6803; A61B 5/6807; A61B 5/681; A61B 5/6843; A61B 5/6844; G06F 1/163; G06F 3/015
(Continued)

(56) References Cited

U.S. PATENT DOCUMENTS 5,064,410 A * 11/1991 Frenkel ................ A61B 5/0531
600/26
5,261,412 A * 11/1993 Butterfield ......... A61B 5/02255
600/485

(Continued)

FOREIGN PATENT DOCUMENTS

EP 2634678 A1 9/2013
EP 3015848 A1 5/2016
(Continued)

OTHER PUBLICATIONS

"Detecting 2 Swipes Without Interrupting Touch", Stack Overflow, Retrieved on May 15, 2018, Webpage available at: https://stackoverflow.com/questions/14400828/detecting-2-swipes-without-interrupting-touch.
(Continued)

*Primary Examiner* — Carl H Layno
*Assistant Examiner* — Michael J Lau
(74) *Attorney, Agent, or Firm* — Harrington & Smith

(57) ABSTRACT

A method, apparatus and computer program, in which a body of a wearable apparatus is maintained maintaining by a link in place at a given part of skin of the user. A sensor platform is movably supported sandwiched between the body and the skin and supported by the body movably with relation to the body towards and away of the skin, when the apparatus is worn by the user. A sensor is supported by the sensor platform. The sensor produces sensor signals corresponding to a property of the skin or underlying matter. The
(Continued)

position of the sensor platform is adjusted by an actuator with relation to the skin.

12 Claims, 2 Drawing Sheets

(52) U.S. Cl.
CPC .......... *A61B 5/6807* (2013.01); *A61B 5/6843* (2013.01); *G06F 1/163* (2013.01); *G06F 3/015* (2013.01)

(58) Field of Classification Search
USPC ........................................................ 600/300
See application file for complete search history.

(56) References Cited

U.S. PATENT DOCUMENTS

| | | | |
|---|---|---|---|
| 5,327,161 A | 7/1994 | Logan et al. | |
| 5,908,027 A * | 6/1999 | Butterfield | A61B 5/021 600/485 |
| 6,132,383 A * | 10/2000 | Chesney | A61B 5/022 600/485 |
| 6,293,904 B1 * | 9/2001 | Blazey | A61B 5/16 600/26 |
| 6,394,959 B1 * | 5/2002 | Takaya | A61B 5/02125 600/485 |
| 6,491,647 B1 * | 12/2002 | Bridger | A61B 5/021 128/900 |
| 6,544,188 B1 * | 4/2003 | Chesney | A61B 5/022 600/500 |
| 6,832,528 B2 * | 12/2004 | Selig | G01G 3/12 73/862.636 |
| 7,598,878 B2 | 10/2009 | Goldreich | |
| 8,641,614 B2 * | 2/2014 | Coelho | A61B 5/0205 600/300 |
| 8,836,648 B2 | 9/2014 | Wilairat | |
| 2004/0150630 A1 | 8/2004 | Hinckley et al. | |
| 2004/0171947 A1 * | 9/2004 | Ogura | A61B 5/02 600/500 |
| 2005/0245839 A1 * | 11/2005 | Stivoric | G06F 19/3418 600/549 |
| 2008/0013777 A1 | 1/2008 | Park et al. | |
| 2008/0262324 A1 * | 10/2008 | Van Der Voort | A61B 5/0059 600/310 |
| 2009/0069648 A1 * | 3/2009 | Irazoqui | A61B 3/16 600/302 |
| 2009/0163787 A1 * | 6/2009 | Mannheimer | A61B 5/14552 600/324 |
| 2009/0278806 A1 | 11/2009 | Duarte et al. | |
| 2010/0240969 A1 * | 9/2010 | Rompa | A61B 5/14542 600/309 |
| 2010/0305416 A1 | 12/2010 | Bedard et al. | |
| 2011/0081037 A1 | 4/2011 | Oh et al. | |
| 2011/0154887 A1 | 6/2011 | Cooper et al. | |
| 2011/0202834 A1 | 8/2011 | Mandryk et al. | |
| 2011/0263950 A1 * | 10/2011 | Larson | G16H 20/10 600/301 |
| 2012/0316448 A1 * | 12/2012 | Gu | A61B 5/02108 600/499 |
| 2014/0022194 A1 | 1/2014 | Ito | |
| 2014/0118281 A1 | 5/2014 | Baker et al. | |
| 2014/0128752 A1 * | 5/2014 | Donaldson | A61B 5/02438 600/490 |
| 2014/0187876 A1 * | 7/2014 | Ohkoshi | A61B 5/0031 600/309 |
| 2014/0275852 A1 * | 9/2014 | Hong | A61B 5/02427 600/301 |
| 2014/0289668 A1 | 9/2014 | Mavrody | |
| 2014/0318699 A1 * | 10/2014 | Longinotti-Buitoni | A61B 5/0002 156/247 |
| 2014/0343389 A1 * | 11/2014 | Goldstein | A61B 5/0022 600/383 |
| 2015/0042588 A1 | 2/2015 | Park | |
| 2015/0366507 A1 * | 12/2015 | Blank | A61B 5/6844 600/340 |
| 2016/0091308 A1 | 3/2016 | Oliaei | |

FOREIGN PATENT DOCUMENTS

| | | |
|---|---|---|
| GB | 2526131 A | 11/2015 |
| GB | 2528055 A | 1/2016 |
| JP | H06178764 A | 6/1994 |
| JP | H09192109 A | 7/1997 |
| JP | 2002224065 A | 8/2002 |
| JP | 2006102191 A | 4/2006 |
| JP | 2007508431 A | 4/2007 |
| JP | 2007512076 A | 5/2007 |
| JP | 2007319343 A | 12/2007 |
| WO | 2005/037918 A1 | 4/2005 |
| WO | 2005/051184 A1 | 6/2005 |
| WO | 2012054828 A2 | 4/2012 |
| WO | WO-2012/054828 A3 | 4/2012 |
| WO | WO-2012054828 A2 * | 4/2012 ............... A61B 5/22 |
| WO | WO 2012054828 A2 * | 4/2012 ............... A61B 5/22 |

OTHER PUBLICATIONS

Wu et al., "Design of the Multi-channel Electroencephalography-based Brain-computer Interface with Novel Dry Sensors", 34th Annual International Conference of the IEEE Engineering in Medicine and Biology Society (EMBC), Aug. 28-Sep. 1, 2012, pp. 1793-1797.
Extended European Search Report received for corresponding European Patent Application No. 14195295.2, dated May 13, 2015, 7 pages.
Non-Final Office action received for corresponding U.S. Appl. No. 14/621,639, dated Apr. 27, 2016, 10 pages.
Final Office action received for corresponding U.S. Appl. No. 14/621,639, dated Dec. 12, 2016, 12 pages.
Non-Final Office action received for corresponding U.S. Appl. No. 14/621,639, dated Jun. 2, 2017, 17 pages.
Final Office action received for corresponding U.S. Appl. No. 14/621,639, dated Feb. 16, 2018, 20 pages.
Office action received for corresponding Japanese Patent Application No. 2017-528438, dated May 7, 2018, 5 pages of office action and 4 pages of translation available.
Office action received for corresponding European Patent Application No. 14195295.2, dated May 8, 2018, 6 pages.
International Search Report and Written Opinion received for corresponding Patent Cooperation Treaty Application No. XXXXX, dated XXXX, XX pages.

* cited by examiner

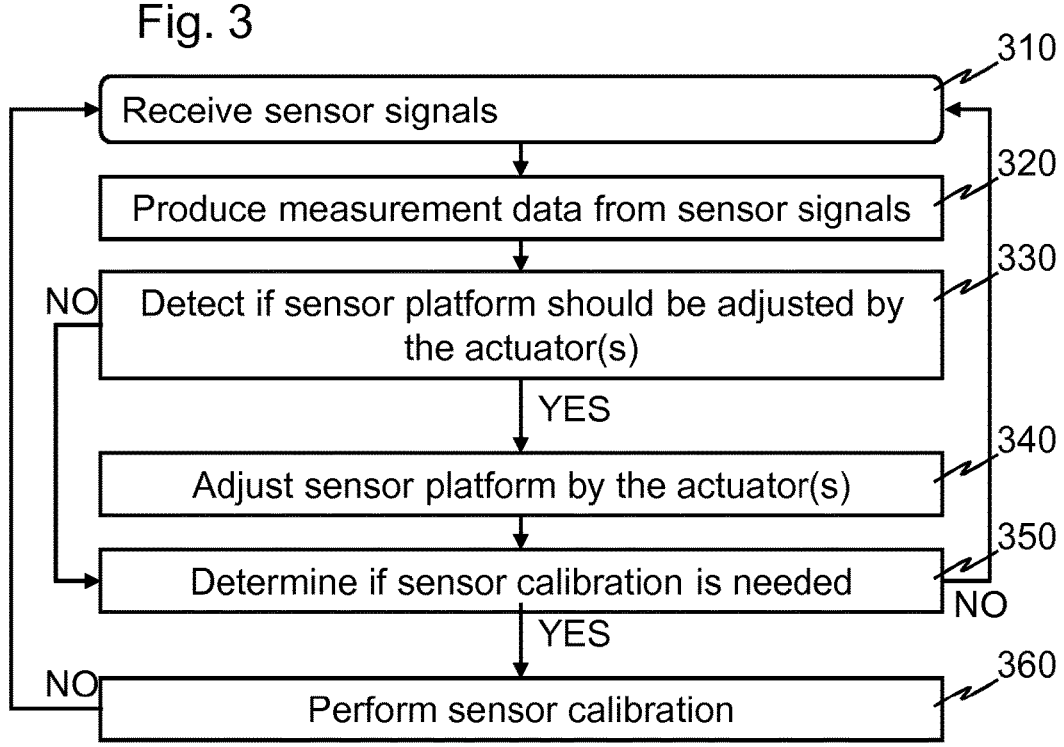

METHOD AND APPARATUS FOR CONTACTING SKIN WITH SENSOR EQUIPMENT

RELATED APPLICATION

This application was originally filed as Patent Cooperation Treaty Application No. PCT/FI2015/050805 filed Nov. 19, 2015 which claims priority benefit to EP Patent Application No. 14195295.2, filed Nov. 28, 2014.

TECHNICAL FIELD

The present application generally relates to contacting skin with sensor equipment.

BACKGROUND

This section illustrates useful background information without admission of any technique described herein representative of the state of the art.

Various metering devices such as pulse sensors have become more common for people to measure their own heart rate, movements or other parameters. A new term quantified self has appeared for the desire to quantify all possible parameters that effect on the physical health of oneself. Metering devices help people measuring themselves for such a purpose, but people who want to measure the effects and control their physical exercise based on pulse, for example.

Pulse measurement is typically performed using a chest strap that is worn under clothes and maintains electric cardiac sensors sensor in place on the skin of the user so that heart beat can be computed from the signals produced by the sensor. The strap is yet awkward to wear and there are companies that have launched or are about to launch wrist worn watch-like pulse sensors, often combined with accelerometers for acting as pedometer.

Some measurements such as optical heart rate measurement require that the sensor is either located at a particular location to which skin access is not convenient to provide in the middle of a day or that the sensor is kept very stably on skin. For the latter need, a device is known that biases a sensor against skin with a spring so as to compensate for shake that would easily otherwise break the contact and prevent reliable measurement.

SUMMARY

Various aspects of examples of the invention are set out in the claims.

According to a first example aspect of the present invention, there is provided an apparatus;
wherein the apparatus is wearable by a user;
the apparatus comprising:
a body;
a link configured to maintain the body in place at a given part of skin of the user;
a sensor platform sandwiched between the body and the skin and supported by the body movably with relation to the body towards and away of the skin, when the apparatus is worn by the user;
a sensor supported by the sensor platform and configured to produce sensor signals corresponding to a property of the skin or underlying matter; and
an actuator configured to adjust the position of the sensor platform with relation to the skin.

The apparatus may further comprise a processor configured to:
receive the sensor signals and to determine suitable compensating movement of the sensor platform from the sensor signals and to cause the actuator to adjust the position of the sensor platform.

The link may be selected from a group consisting of: a strap; a belt; a sock; a shoe; a headphone frame; a frame of eyeglasses or sun glasses; a sleeve or a collar of a shirt or pullover; and a waistband of trousers or skirt.

The actuator may be configured to compensate centrifugal forces acting move the sensor away from the skin.

According to a second example aspect of the present invention, there is provided a method comprising:
maintaining by a link a body of a wearable apparatus in place at a given part of skin of the user;
movably supporting a sensor platform sandwiched between the body and the skin and supported by the body movably with relation to the body towards and away of the skin, when the apparatus is worn by the user;
supporting a sensor by the sensor platform and producing sensor signals corresponding to a property of the skin or underlying matter; and adjusting by an actuator the position of the sensor platform with relation to the skin.

The method may further comprise receiving the sensor signals and determining suitable compensating movement of the sensor platform from the sensor signals and causing the actuator to adjust the position of the sensor platform.

The link may be selected from a group consisting of: a strap; a belt; a sock; a shoe; a headphone frame; a frame of eyeglasses or sun glasses; a sleeve or a collar of a shirt or pullover; and a waistband of trousers or skirt.

The method may further comprise compensating by the actuator centrifugal forces acting move the sensor away from the skin.

According to a third example aspect of the present invention, there is provided a computer program comprising computer executable program code configured to control a wearable device, when the computer executable program code is executed, to:
receive sensor signals corresponding to a property of skin or underlying matter from a sensor supported by a movably supported sensor platform that is adjustable with relation to a body of the wearable device with an actuator towards or away of skin of the user;
determine whether the sensor platform should be moved by the actuator; and
adjust by an actuator the position of the sensor platform with relation to the skin so that the operation of the sensor is enhanced.

The enhancing of the operation of the sensor may comprise reducing pressing of the sensor platform against the skin so that blood flow obstruction is reduced.

The computer program may be stored in a computer readable memory medium.

Any foregoing memory medium may comprise a digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

According to a fourth example aspect of the present invention, there is provided an apparatus comprising a memory and a processor that are configured to cause the apparatus to perform the method of the first example aspect.

According to a fifth example aspect of the present invention, there is provided an apparatus comprising a memory and a processor that are configured to cause the apparatus to perform the method of the second example aspect.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which:

FIG. 3 shows a flow chart of a process of an example embodiment.

DETAILED DESCRIPTION OF THE DRAWINGS

Figure 1:
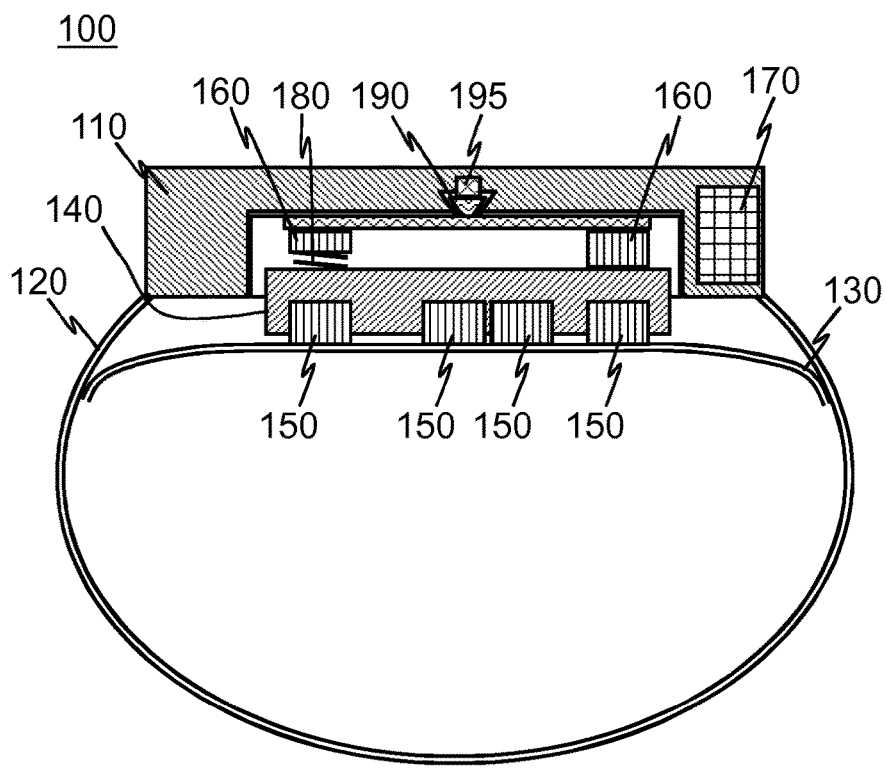
FIG. 1 shows an architectural drawing of a system of an example embodiment.
Figure 2:
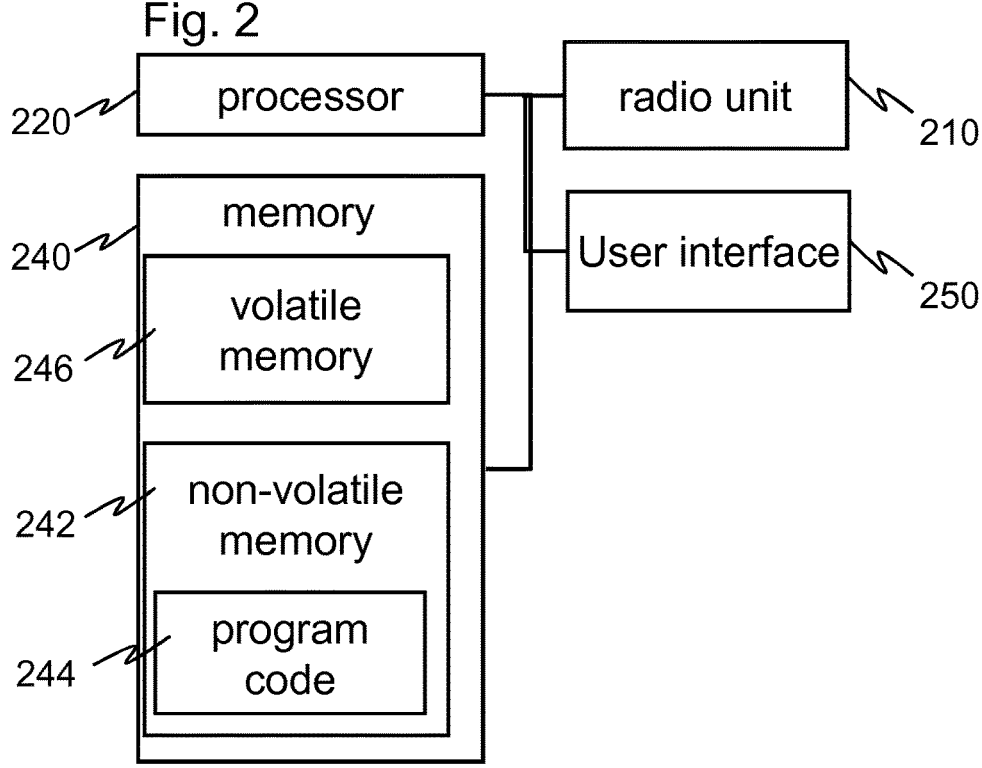
FIG. 2 shows a block diagram of the apparatus 200 of an example embodiment.

An example embodiment of the present invention and its potential advantages are understood by referring to FIGS. 1 through 3 of the drawings. In this document, like reference signs denote like parts or steps.

FIG. 1 shows a schematic drawing of an apparatus 100 of an example embodiment. In FIG. 1, the apparatus 100 is a wearable device that is shaped like a watch and it may be configured to display time. The apparatus comprises a body 110 that is made of any of metals; plastics; carbon fiber materials; glass; wood; ceramics; and any combination or composition thereof. The body 110 of the apparatus 100 can be formed roughly as a concave block or unit or as a block or unit with a cut-out on one side thereof. The apparatus 100 further comprises a link 120 configured to maintain the body 110 in place at a given part of skin 130 of a user of the device. In FIG. 1, the body 110 is, the scale is exaggerated. In an example embodiment, at least by some portions of the body are in engagement with the skin 130. Using FIG. 1 as an example, the leftmost and rightmost parts of the body 110 reach in an example embodiment to the skin 130 and engage against the skin 130.

In the example of FIG. 1, the link 120 is a watch strap. The apparatus 100 further comprises a sensor platform 140 that sandwiched between the body 110 and the skin 130. The sensor platform 140 is supported by the body 110 movably with relation to the body 110 towards and away of the skin 130, when the apparatus is worn by the user. The apparatus 100 further comprises a sensor 150 supported by the sensor platform 140 and configured to produce sensor signals corresponding to a property of the skin or underlying matter (capillaries and veins, for example); and an actuator 160 configured to adjust the position of the sensor platform with relation to the skin. The apparatus 100 further comprises a processor 170 configured to receive the sensor signals (through connections not shown in FIG. 1) and to determine suitable compensating movement of the sensor platform 140 from the sensor signals and to cause the actuator 160 to adjust the position of the sensor platform 140.

In an example embodiment, the sensor 150 is formed of two or more parts. For example, the sensor 150 may comprise a transmitter (of light, for example) and a receiver that are within same of different physical units carried by the sensor platform 140.

Various kinds of apparatuses are provided in different embodiments. The link can be selected from a wide variety of different structures to suit the desired implementation. In an example embodiment, the link is selected from a group consisting of: a strap; a belt; a sock; a shoe; a headphone frame; a frame of eyeglasses or sun glasses; a sleeve or a collar of a shirt or pullover; and a waistband of trousers or skirt. It is notable that in an example embodiment, the link is not permanently connected to the body 110. For example, in a watch form implementation, the straps can be user replaceable. As another example, the body can be linked to rest against the skin 130 by a piece of clothing such as a sock or underwear clothing so that a surrounding portion of (preferably flexible) clothing links the body to the skin 130.

In an example embodiment, the actuator 160 is configured to compensate centrifugal forces acting move the sensor away from the skin. It is observed, that spring-loaded sensor contacting with skin is prone to error as a) it may be left too loose so that the measurement does not function reliably (ambient light leaks in or optical emitter light does not properly penetrate through the skin in case of optical measurement) and b) it may get too tight so that the sensor interferes normal blood flow in underlying fine veins being measured. In an example embodiment, a resilient member or spring 180 is provided to help the sensor 150 to maintain its contact with the skin 130 while the actuator 160 is configured to adjust the distance of the sensor platform 140 from the skin 130. In this case, the distance adjustment may refer to adjusting average distance if the distance can slightly vary due to resilient biasing of the sensor platform against the skin 130, or the distance adjustment may be caused by slightly squeezing the skin 130 and underlying matter by the sensor 150, if the sensor 150 protrudes from the exterior surface of the sensor platform 140.

FIG. 1 shows gaps on both lateral sides of the sensor platform 140 between the sensor platform 140 and the body 110. In an example embodiment, the sensor platform 140 is formed of a rear wall of a cover that forms the body 110. This can be implemented, for example, by forming the cover of suitably flexible material or by forming a flexible seam between the sensor platform and surround parts of the body 110. With a cover that forms both the body 110 around the sensor platform 140 and the sensor platform 140, a barrier can be formed against entry of dust and water to the interior of the apparatus 100.

In an example embodiment, the body 110 comprises a flexible rear wall (not shown) that is configured to act as the resilient member or spring 180 and the actuator as well as the sensor platform are sandwiched between the flexible rear wall of the body and the skin, when the apparatus is worn by the user.

In an example embodiment, there are two or more separately actuated sensor areas having transmitters or receivers for same or different function. For example, photoplethysmogram measurement parts may require lighter contact than a galvanic measurement part or a thermometer. In an example embodiment, separately actuated sensors 150 are supported by same sensor platform 140. For example, different actuators 160 and sensors 150 can be positioned near distant edges of the sensor platform 140.

In an example embodiment, the sensors 150 have a lateral float 190 with respect to their support (e.g. watch body). The lateral float comprises, for example, a resilient support and/or a slidable of pivotable support. In an example embodiment, the lateral float comprises one or more of any of: a spring; a magnet; and an actuator; a piezoelectric actuator; a shape memory alloy actuator; and a solenoid-coil actuator. FIG. 1 shows a slidably supporting lateral float 190 and a lateral actuator 195 such as a linear motor. The lateral actuator 195 can enhance reliability/accuracy of the photoplethysmogram, for example. Moreover, in an embodiment with a lateral float 190, contacting parts (such galvanic skin response and/or thermometering parts) that are pressed with greater force against the skin may also help to anchor the sensor platform 140 and the sensors 150 with relation to the skin. This can enhance accuracy of measurements with sensors 150 that are prone to errors on lateral shifting against the skin 130. Notice that FIG. 1 shows the lateral float in direction of an arm of the person who wears the watch-shaped apparatus 100 in part for ease of illustration. In another example embodiment, the lateral float is implemented in another direction such as perpendicularly to the arm of the user. Generally, the lateral float may be arranged to enable compensation of largest lateral movements of the sensors 150 with relation to the skin 130.

In an example embodiment, the sensor platform is rotatably supported to the body by a sparse thread or by lugs engaging to one or more sloping grooves. In this example embodiment, the actuator is formed using shape memory allow wire that is configured to rotate, on shrinking by length, the sensor platform so that the sensor platform turns and by rotation ascends or descends with relation to the body as forced by the thread or sloping groove(s). A movement return spring can be provided to act against the shape memory alloy wire so as to rotate back the sensor platform when the shape memory alloy wire length increases.

In an example embodiment, the control of the contact actuation can be performed purely based on measured signals i.e. without dedicated sensing of pressure, for example. The control can be performed on demand only. Hence, the adjustment can be performed with few power-consuming movements of the sensors. In an example embodiment, the adjustments are defined taking into account the received temporary and averaged signals and/or the mode of operation of the host device. For example, the adjustments can be defined depending on which of many different measurements are currently being needed and how narrow or broad tolerance they allow for the skin contact adjustment. In an example embodiment, the adjustment is performed so that no power is drawn except during the adjustment.

In another example embodiment, the control of the contact actuation is performed using a pressure, contacting force (or load) or contact measurement. For example, the apparatus may comprise a fluid-filled (e.g. gas such as air or nitrogen; liquid such as water or oil; emulsion such as liquid fat and air or nitrogen) resilient element 180 and its fluid pressure may be measured. A force sensor can be implemented using, for example, a load cell (e.g., piezoelectric load cell, hydraulic load cell, pneumatic load cell). The contact sensor can be implemented, for example, optically (for example, measuring incoming ambient light) acoustically by measuring an acoustic response to audio transmission (in ultrasound range, for example), galvanic (measuring conductivity difference of two pads of known different sizes and determining from their mutual values the likely contacting area proportions). In an example embodiment, the adjustment moves an entire sensor platform or sub-frame along a predetermined track (for example, linearly or along an arcuate track). In an example embodiment, the adjustment moves each of two or more sides of the sensor platform so that the angle and/or track of the movement of the platform with relation to the host device changes or remains constant.

In an example embodiment, the actuator 160 is formed using two or more serially connected element.

In an example embodiment, the actuator 160 comprises a resilient member functionally in series with a position moving part so that the actuator can adjustably change position of an actuated part while providing some resilience in the positional adjustment.

In an example embodiment, the actuatably movable sensor(s) 150 can be calibrated to operate reliably in the contact provided by the actuator(s). In case of photoplethysmogram, the calibration can involve, for example, determining threshold levels for different phases of heart beat caused blood flow (e.g., percentage of sensor reading that indicates heat beat start and percentage of sensor reading that indicates heart beat end). In an example embodiment, there is another control loop for adapting the operation of the actuation to improve sensor operation followed by re-calibration of the sensor 150. The adaptation of the actuation can be performed to reduce the need of actuation movements. In an example embodiment, the user is allowed to indicate a desire to increase or decrease the pressure of the sensor(s) against her skin and this indication is used to automatically adapt the actuation.

It should be understood that in movement of two parts with relation to another, either or both parts can be seen to be moving. For example, in the described embodiment in which a watch formed apparatus has a strap attached to a cover or body surrounding the sensor platform, it can be logically understood that the strap holds the body substantially in place while the sensor platform moves with relation to both the skin and the body of the apparatus. However, the sensor platform is equally movable with relation to the body of the apparatus if the sensor platform is attached to the straps or link mechanism in general and the actuator moves the body with relation to the sensor platform. Also in that case, the sensor platform is movable with relation to the body of the apparatus. By using the actuator to moving the sensor platform with relation to the body, the body can engage to the skin with increasing or decreasing force and thus cause that the actuator also adjusts the position of the sensor platform with relation to the skin.

The apparatus can be formed in a great variety of different kinds of host devices such as in: a belt buckle; a watch; headset; an eyeglass frame connection; an ankle strap; a shoe heel; and a transplant. Moreover, various kinds of actuators are usable.

FIG. 2 shows a block diagram of the apparatus 200 of an example embodiment, for helping understanding of various processing and control related aspects. The apparatus 200 can be suited for use as the apparatus 100.

The apparatus 200 comprises a memory 240 including a persistent memory 242 that stores computer program code 244 (e.g. applications and operating system) and a volatile memory or work memory 246. The persistent or non-volatile memory 242 is formed using, for example, one or more of: read only memory; flash-random access memory; optical memory; magnetic memory; hard disk drive; and synchronous dynamic random access memory. The work memory is formed, for example, of a random access memory; synchronous dynamic random access memory; and/or double data rate synchronous dynamic random access memory. The apparatus 200 further comprises a processor 220 for controlling the operation of the apparatus 200 by running the computer program code 242 in the work memory 246. The apparatus 200 further comprises a radio unit 210 for communicating with the cellular network 120. The radio unit 210 comprises, for example, a Universal Mobile Telecommunications System communication unit; a long-term evolution radio unit; or satellite data communication unit. The processor 220 comprises, for example, any one or more of: a master control unit; a microprocessor; a digital signal processor; an application specific integrated circuit; a field programmable gate array; and a microcontroller. The apparatus 200 further comprises a subscriber identity module 250.

FIG. 3 shows a flow chart of a process of an example embodiment. The process comprises: receiving 310 sensor signals; producing measurement result data based on the sensor signals 320 for health or exercise monitoring, for example; determine 330 from the sensor signals 320 whether the sensor platform 140 should be adjusted by the actuator 160 and adjusting 340 the sensor platform if necessary; determining 350 form the sensor signals whether the sensor 150 should be calibrated and if yes; calibrating 360 the sensor 150 with suitable actuator action (e.g. varying the position of the sensor platform 140 to perform measurements with different positions). The adjusting 340 of the sensor platform may comprise either or both adjusting the sensor platform 140 towards or away of the skin 130 and laterally adjusting the sensor platform 140.

Without in any way limiting the scope, interpretation, or application of the claims appearing below, a technical effect of one or more of the example embodiments disclosed herein is that the contact of a sensor with the skin can be automatically adapted according to the real needs of the measurement that the sensor performs so that the contact need not be inconveniently hard nor harmful for the measurement. Another technical effect of one or more of the example embodiments disclosed herein is that the automatic adaptation of the contact may help to avoid undue blockage of underlying capillaries. Another technical effect of one or more of the example embodiments disclosed herein is that the automatic adaptation of the contact may enable obtaining sufficient frictional support from the skin to inhibit lateral movement of the sensor in relation to the skin. Another technical effect of one or more of the example embodiments disclosed herein is that the automatic adaptation of the contact may enhance reliability of calibration of measurement with the sensor.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. A sensor structure for a user wearable apparatus, the sensor structure comprising:
a sensor platform configured to be sandwiched between a body of the user wearable apparatus and skin of a user, where the sensor platform is configured to be supported on the body of the user wearable apparatus proximate a connection to be movable with relation to the body of the user wearable apparatus towards and away of the skin when the sensor structure is mounted to the user wearable apparatus and the user wearable apparatus is worn by the user;
a sensor supported on the sensor platform and configured to produce sensor signals corresponding to a property of the skin or underlying matter;
an actuator located on the sensor platform, where the actuator is configured to be located proximate the connection of the sensor platform to the user wearable apparatus, and where the actuator is configured to adjust position of the sensor platform towards and away of the skin;
a processor configured to receive the sensor signals and to determine suitable compensating movement of the sensor platform from the sensor signals and to cause the actuator to adjust the position of the sensor platform to prevent the sensor from moving away from the skin; and
a lateral float configured to enable lateral movement of the sensor platform with relation to the body, where the lateral float is configured to inhibit lateral movement of the sensor with relation to the skin.

2. The sensor structure of claim 1, further comprising a lateral actuator configured to compensate lateral movement of the body with relation to the skin.

3. The sensor structure of claim 1, wherein the actuator is configured to compensate centrifugal forces acting to move the sensor away from the skin.

4. An apparatus comprising:
a body;
a sensor platform configured to be sandwiched between the body of the apparatus and skin of a user, where the sensor platform is movably supported by the body proximate a connection of the sensor platform to the body towards and away of the skin when the apparatus is worn by the user;
a sensor supported on the sensor platform and configured to produce sensor signals corresponding to a property of the skin or underlying matter;
an actuator located between the sensor platform and the body, where the actuator is configured to adjust position of the sensor platform towards and away of the skin;
a processor configured to receive the sensor signals and to determine suitable compensating movement of the sensor platform from the sensor signals and to cause the actuator to adjust the position of the sensor platform to prevent the sensor from moving away from the skin; and
a lateral float configured to enable lateral movement of the sensor platform with relation to the body, where the lateral float is configured to inhibit lateral movement of the sensor with relation to the skin.

5. The apparatus of claim 4, further comprising a link configured to maintain the body in place at a given part of skin of the user.

6. The apparatus of claim 4, further comprising a lateral actuator configured to compensate lateral movement of the body with relation to the skin.

7. The apparatus of claim 4, wherein the actuator is configured to compensate centrifugal forces acting to move the sensor away from the skin.

8. A method comprising:
maintaining by a link a body of a wearable apparatus in place at a given part of skin of a user;
movably supporting a sensor platform, sandwiched between the body and the skin, on the body of the wearable apparatus, where the sensor platform is supported by the body movably with relation to the body towards and away of the skin when the wearable apparatus is worn by the user;
supporting a sensor on the sensor platform and producing sensor signals corresponding to a property of the skin or underlying matter; and
adjusting by an actuator position of the sensor platform, where the actuator is located between the sensor platform and the body, and where the adjusting adjusts the position of the sensor towards and away of the skin to assist in maintaining contact of the sensor to the skin as a portion of the body moves towards and away of the skin, where the adjusting comprises a processor receiving the sensor signals and determining suitable compensating movement of the sensor platform from the sensor signals and to cause the actuator to adjust the position of the sensor platform to prevent the sensor from moving away from the skin,
where a lateral float enables lateral movement of the sensor platform with relation to the body so as to inhibit lateral movement of the sensor with relation to the skin.

9. The method of claim 8, further comprising a lateral actuator configured to compensate lateral movement of the body with relation to the skin.

10. The method of claim 8, further comprising compensating by the actuator centrifugal forces acting to move the sensor away from the skin.

11. A computer readable medium encoded with computer program comprising computer executable program code configured to control a wearable device, when the computer executable program code is executed, to:
receive sensor signals corresponding to a property of skin or underlying matter from a sensor supported by a movably supported sensor platform that is adjustable with relation to a body of the wearable device with an actuator towards or away of skin of the user;
determine whether the sensor platform should be moved by the actuator;
adjust by the actuator the position of the sensor platform with relation to the skin so that the operation of the sensor is enhanced, where the actuator is located between the sensor platform and the body, and where the adjusting adjusts the position of the sensor towards and away of the skin to assist in maintaining contact of the sensor to the skin as a portion of the body moves towards and away of the skin, where the adjusting comprises a processor receiving the sensor signals and determining suitable compensating movement of the sensor platform from the sensor signals and to cause the actuator to adjust the position of the sensor platform to prevent the sensor from moving away from the skin, where lateral movement of the sensor platform with relation to the body is enabled with a lateral float so as to inhibit lateral movement of the sensor with relation to the skin; and
control a lateral actuator with use of the processor to compensate lateral movement of the body with relation to the skin so as to inhibit lateral movement of the sensor with relation to the skin.

12. The computer readable medium of claim 11, wherein the enhancing of the operation of the sensor may comprise reducing pressing of the sensor platform against the skin so that blood flow obstruction is reduced.

* * * * *